United States Patent
Terry et al.

(10) Patent No.: US 10,610,163 B2
(45) Date of Patent: Apr. 7, 2020

(54) ASSESSING SUSCEPTIBILITY TO EPILEPSY AND EPILEPTIC SEIZURES

(71) Applicants: UNIVERSITY OF EXETER, Exter Devon (GB); KINGS COLLEGE LONDON, London (GB)

(72) Inventors: John Robert Terry, Exeter (GB); Mark Richardson, London (GB); Oscar Benjamin, Bristol (GB)

(73) Assignees: UNIVERSITY OF EXETER, Exeter Devon (GB); KINGS COLLEGE LONDON, London (GB)

( * ) Notice: Subject to any disclaimer, the term of this patent is extended or adjusted under 35 U.S.C. 154(b) by 1195 days.

(21) Appl. No.: 14/406,452

(22) PCT Filed: Jun. 5, 2013

(86) PCT No.: PCT/GB2013/051485
§ 371 (c)(1),
(2) Date: Dec. 8, 2014

(87) PCT Pub. No.: WO2013/182848
PCT Pub. Date: Dec. 12, 2013

(65) Prior Publication Data
US 2015/0164431 A1 Jun. 18, 2015

Related U.S. Application Data

(60) Provisional application No. 61/656,121, filed on Jun. 6, 2012.

(30) Foreign Application Priority Data

Jun. 6, 2012 (GB) .................................. 1209975.0

(51) Int. Cl.
*A61B 5/00* (2006.01)
*G01R 33/48* (2006.01)
(Continued)

(52) U.S. Cl.
CPC .......... *A61B 5/7275* (2013.01); *A61B 5/0476* (2013.01); *A61B 5/4094* (2013.01);
(Continued)

(58) Field of Classification Search
CPC ... A61B 5/7275; A61B 5/0476; A61B 5/7264; A61B 5/7246; A61B 5/4848;
(Continued)

(56) References Cited

U.S. PATENT DOCUMENTS 8,679,009 B2 * 3/2014 Osorio ................. A61B 5/4094
600/300
8,951,189 B2 * 2/2015 Osorio ................. A61B 5/4094
600/300
(Continued)

FOREIGN PATENT DOCUMENTS

WO 2011088227 A1 7/2011

OTHER PUBLICATIONS

A plenomenological model of seizure initiation suggests network structure may explain seizure frequency in idiopathic generalised epilepsy Benjamin O; Fitzgerald T H; Ashwin P; Tsaneva-Atanasova K; Chowdhury F; Richardson M P; Terry J R The Journal of Mathematical Neuroscience (JMN) Date: Jan. 6, 2012.
(Continued)

*Primary Examiner* — Angela M Hoffa
(74) *Attorney, Agent, or Firm* — King & Schickli, PLLC

(57) ABSTRACT

Assessing Susceptibility to Epilepsy and Epileptic Seizures A method and system adapted to assist with assessing susceptibility to epilepsy and/or epileptic seizures in a patient receives (202) patient brain data and generates (204) a network model from the received patient brain data. The system further generates (206) synthetic brain activity data in at least some of the nodes of the network model and computes (208) seizure frequency from the synthetic brain
(Continued)

activity data by monitoring transitions from non-seizure states to seizures states in at least some of the nodes over time. The system further includes a device (104, 110) configured to use the seizure frequency to compute (210) a likelihood of susceptibility to epilepsy and/or epileptic seizures in the patient, and a device (104, 110) configured to compare (212) the computed likelihood with another likelihood of susceptibility to epilepsy and/or epileptic seizures in order to assess whether the likelihood has increased or decreased.

15 Claims, 1 Drawing Sheet

(51) Int. Cl.
*G16H 50/30* (2018.01)
*G16H 50/50* (2018.01)
*A61B 5/0476* (2006.01)
*A61B 5/04* (2006.01)

(52) U.S. Cl.
CPC .......... *A61B 5/4848* (2013.01); *A61B 5/7246* (2013.01); *A61B 5/7264* (2013.01); *G01R 33/4806* (2013.01); *G16H 50/30* (2018.01); *G16H 50/50* (2018.01); *A61B 5/04004* (2013.01); *A61B 5/04008* (2013.01)

(58) Field of Classification Search
CPC .............. A61B 5/4094; A61B 5/04008; A61B 5/04004; G01R 33/4806; G06F 19/3431; G06F 19/3437
See application file for complete search history.

(56) References Cited

U.S. PATENT DOCUMENTS

| | | | | |
|---|---|---|---|---|
| 8,951,192 | B2* | 2/2015 | Osorio | A61B 5/4094 600/300 |
| 9,504,390 | B2* | 11/2016 | Osorio | A61B 5/0205 |
| 2006/0111644 | A1* | 5/2006 | Guttag | A61B 5/048 600/544 |
| 2006/0200038 | A1* | 9/2006 | Savit | A61B 5/0476 600/544 |
| 2007/0149952 | A1* | 6/2007 | Bland | G06F 19/345 604/890.1 |
| 2008/0082019 | A1* | 4/2008 | Ludving | A61B 5/04004 600/544 |
| 2008/0183097 | A1 | 7/2008 | Leyde | |
| 2009/0281446 | A2* | 11/2009 | Ludvig | A61B 5/04004 600/544 |
| 2010/0023089 | A1* | 1/2010 | DiLorenzo | A61B 5/04001 607/45 |
| 2011/0319785 | A1* | 12/2011 | Snyder | A61B 5/0006 600/544 |

OTHER PUBLICATIONS

A stochastic framework for evaluating seizure prediction algorithms using hidden Markov models Wong S; Gardner A B; Krieger A M; Litt B Journal of NeurophysiologyPublished Mar. 1, 2007 vol. 97 No. 3, 2525-2532 DOI: 10.1152/jn.00190.2006 XP002712913.
Brain Network Topology Determines the Emergence of Seizures in Focal and Generalized Epilepsies Wessel Woldman; Helmut Schmidt; Adam Pawley; Eugenio Abela; Mark P. Richardson; John R. Terry; United Kingdom; unpublished.

* cited by examiner

ASSESSING SUSCEPTIBILITY TO EPILEPSY AND EPILEPTIC SEIZURES

FIELD OF THE INVENTION

The present invention relates to assessing susceptibility to epilepsy and/or epileptic seizures.

BACKGROUND OF THE INVENTION

Epilepsy is the commonest serious neurological disease, affecting 1.2% of the population in the UK. Epilepsy is often mistakenly viewed as easily treated, whereas, in fact, 40% of new-onset epilepsy remains uncontrolled after one year of antiepileptic drug (AED) treatment, and over 30% of people with epilepsy never respond to treatment, with consequent morbidity and mortality. Epilepsy is directly responsible for over 1000 deaths per year in the UK, and is the $5^{th}$ most common cause of avoidable years of life lost in men and $8^{th}$ in women. It is the leading cause of repeated unplanned admissions to NHS hospitals, and is estimated to cost the EU 15.5 billion euros per annum.

Currently, the diagnosis of epilepsy in a patient is usually based on a subjective interpretation by clinicians of descriptions of the seizure from the patient and witnesses, coupled with similarly subjective interpretation of features within EEG readings, MRI and CT scans, etc. In some instances, simultaneous video and EEG during prolonged recordings or using provocation may enable a seizure fortuitously to be directly observed, but simultaneous video-EEG is costly, not widely available, and fortuitously recording a seizure is unfeasible for most patients. Epilepsy is generally only considered as a diagnosis after a patient has suffered at least two attacks, and even after two or more attacks the diagnosis may remain uncertain, meaning that the prescription of anti-epileptic drugs is delayed. There are commercially available software packages which analyse data from prolonged EEG recordings and detect the presence of epileptiform spikes or seizures within this data. This allows clinicians reviewing the data to identify any epileptic events undergone by the patient which may not have had an external physical manifestation. This type of software is generally used for the monitoring of patients previously diagnosed with epilepsy, rather than as a diagnostic tool, and if used as a diagnostic would still require interpretation by a clinician of the events observed.

The assessment of the efficacy of anti-epileptic medication is essentially a trial-and-error process, with patients being prescribed what is thought to be an appropriate AED for the diagnosed epileptic syndrome, and then monitored for a decrease or cessation of seizures. If seizures continue without decrease, the patient must be prescribed a second AED and the process is repeated. Assessing treatment in this conventional manner means that patients can continue to have seizures for many months after initial diagnosis.

The clinical expression of seizures requires the involvement of large-scale brain networks, in order to create behavioural output and/or to allow subjective experience; since without behavioural or subjective features, there is no epilepsy. Seizures emerge rapidly from normal activity of brain networks and usually self-terminate; the timescale of onset and offset of a seizure is orders of magnitude faster than any plausible change in the numbers of neurons, axons, dendrites or synapses, and many other neuronal mechanisms. Therefore, the neuronal machinery causing seizures is the same machinery present in the brain interictally during normal function. The dynamic behaviour of a complex network is not predictable through studying the properties of individual small-scale components of the system. This means that the dynamic emergence of seizures in the complex system of the brain cannot be fully explained by studying, e.g. ion channels, individual neurons or brain slices.

SUMMARY OF THE INVENTION

Embodiments of the present invention are intended to address at least some of the abovementioned problems. Embodiments allow a degree of certainty to be assigned to each case with regards to whether epilepsy can be diagnosed, even after the first attack. Embodiments can act as a prognostic tool for remission, as any change in the value of the 'seizure susceptibility' score in response to treatment can be easily monitored through analysis of patient brain data. Embodiments can act as a predictor of the efficacy of a particular AED over a much more rapid timescale than current methods, as any change in the value of the 'seizure susceptibility' score in response to treatment can be easily monitored through analysis of patient brain data. Embodiments can also be used to help study the timescales involved in the lowering of the seizure susceptibility score when the epilepsy becomes well controlled. Embodiments can give a statistical probability of seizure, based on a computational model of the results of analysis of brain data. This can change the diagnostic and prognostic techniques from a subjective, clinical evaluation to an objective, quantitative calculation. Once generalised epilepsy has been diagnosed and drug treatment has been started, the effect of a prescribed drug on the seizure susceptibility can be measured, giving an indication of whether the drug is working or not. Embodiments can take routine brain data from periods of time during which no seizures occur and use it to predict the likelihood of seizure.

According to a first aspect of the present invention there is provided a system adapted to assist with assessing susceptibility to epilepsy and/or epileptic seizures in a patient, the system including or comprising:

a device configured to receive patient brain data;

a device configured to generate a network model from received patient brain data, wherein nodes in the network model correspond to brain regions of the patient brain data and connections between the nodes of the network model correspond to measured connections between the brain regions;

a device configured to generate synthetic brain activity data in at least some of the nodes of the network model;

a device configured to compute seizure frequency from the synthetic brain activity data by monitoring transitions from non-seizure states to seizures states in at least some of the nodes over time;

a device configured to use the seizure frequency to compute a likelihood of susceptibility to epilepsy and/or epileptic seizures in the patient, and a device configured to compare the computed likelihood with another likelihood of susceptibility to epilepsy and/or epileptic seizures in order to assess whether the likelihood has increased or decreased.

The synthetic brain activity data may describe a transition of a said node from interictal to ictal states. The network model may include a discrete set of nodes with irregular directional connectivity, where properties of each said node are described by a mathematical equation that simultaneously permits a normal resting state and a high-amplitude oscillatory state.

The patient brain data may comprise EEG data. The nodes of the network model may be based on interdependencies between EEG signals from different recording electrodes or brain regions.

The patient brain data may comprise MRI data. The nodes of the network model may be based on parcellating grey-matter regions of the patient brain data. The network model may be based on interdependencies between MRI signals from different brain regions. The network model can be inferred from the patient data using a beta weights method, or by using a measure of nonlinear correlation.

The synthetic brain activity data may be generating using a dynamic computational model based on features of human seizure data, e.g. a model that phenomenologically or physiologically models transitions from interictal to ictal states in brain regions over time. Alternatively, the synthetic brain activity data can be generated using a probabilistic model, for example, representation by a Markov process.

The seizure frequency may describe a rate of transition of a said node within the network model, or an average of transitions across all said nodes of the network model per unit of synthetic brain activity data generation time. Alternatively, the seizure frequency can be based on an average value across all nodes of time spent in a dynamic region corresponding to the seizure states of the model per unit of synthetic brain activity data generation time.

The further likelihood may correspond to a historical computed likelihood. The likelihood compared with the historical computed likelihood may be computed following AED treatment.

According to another aspect of the present invention here is provided a brain data recording machine, such as an EEG machine, including a system substantially as described herein. The brain data recording machine can obtain the patient brain data.

According to another aspect of the present invention there is provided a method of assisting with assessing susceptibility to epilepsy in a patient, the method including or comprising:

receiving patient brain data;

generating a network model from received patient brain data, wherein nodes in the network model correspond to brain regions of the patient brain data and connections between the nodes of the network model correspond to measured connections between the brain regions;

generating synthetic brain activity data in at least some of the nodes of the network model;

computing seizure frequency from the synthetic brain activity data by monitoring transitions from non-seizure states to seizures states in at least some of the nodes over time;

using the seizure frequency to compute a likelihood of susceptibility to epilepsy and/or epileptic seizures in the patient, and comparing the computed likelihood with another likelihood of susceptibility to epilepsy and/or epileptic seizures in order to assess whether the likelihood has increased or decreased.

According to other aspects of the present invention there are provided computer program elements comprising: computer code means to make the computer execute methods substantially as described herein. The element may comprise a computer program product.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. As such, many modifications and variations will be apparent to practitioners skilled in the art. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

BRIEF DESCRIPTION OF THE DRAWING FIGURES

The invention may be performed in various ways, and, by way of example only, embodiments thereof will now be described, reference being made to the accompanying drawings in which.

DETAILED DESCRIPTION OF THE INVENTION

Figure 1:
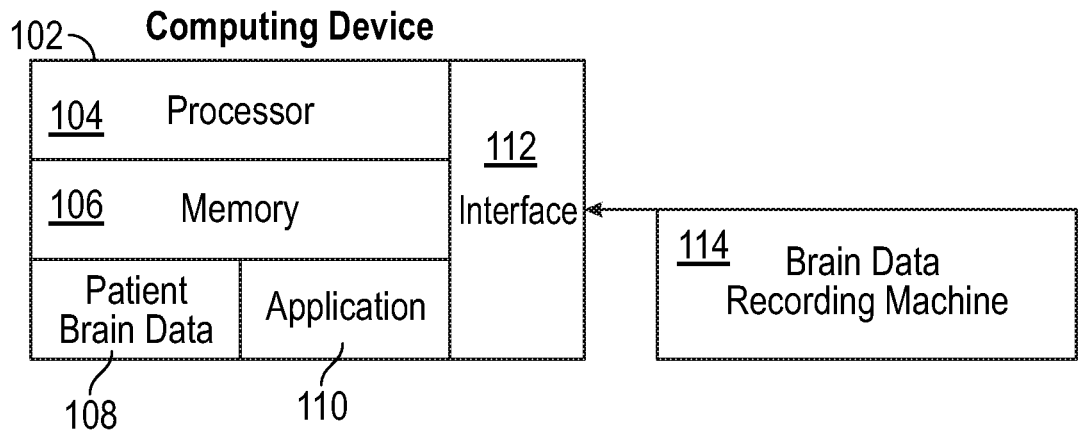
FIG. 1 is a schematic illustration of an example system.

FIG. 1 shows a computing device 102 including a processor 104 and memory 106. The memory includes patient brain data 108 and an application 110 for processing the patient brain data. The computing device further includes an interface 112 for communicating with remote devices. The computing device can also have other conventional features, such as a display, user-interface, etc, that need not be described herein in detail.

In the example system, the interface 112 of the computing device is connected to a brain data recording machine 114, which may be an EEG machine, MEG machine, MRI scanner, or the like. In the example the application 110 is configured to receive data 108 from the machine 114 (via any wired or wireless data transfer medium) and process it as described below. In other embodiments, the brain data 108 may be received by the computing device in another manner, e.g. over a communications network or from trans-portable storage medium, such as a DVD. It will be further understood that in alternative embodiments, at least some of the steps of the application 110 may be performed sequentially, on in parallel, on one or more remote processing devices.

Figure 2:
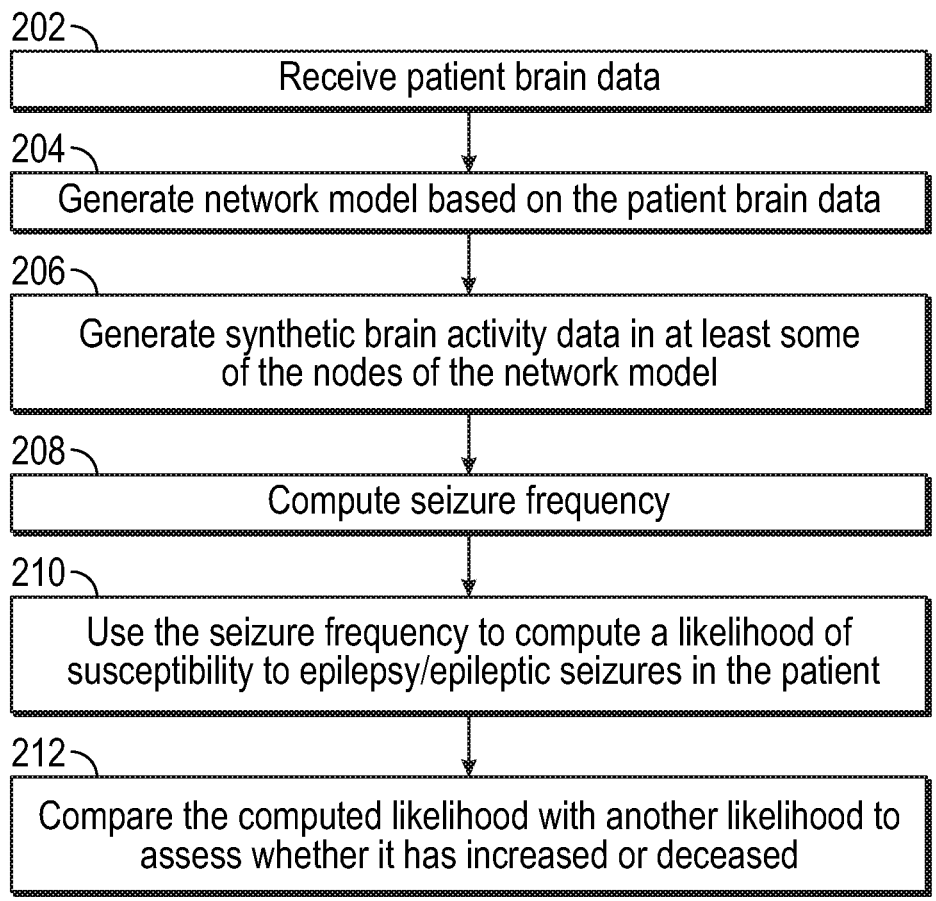
FIG. 2 is a flowchart illustrating steps performed by a computing device of the system.

FIG. 2 illustrates schematically steps, performed by an example of the application 110. The skilled person will understand that the steps can be coded using any suitable programming language and/or data structures. It will also be understood that in alternative embodiments some of the steps may be omitted and/or re-ordered and/or additional steps may be performed.

At step 202, the application 110 receives patient brain data from a source as described above. At step 204, the application generates a network model based on the patient brain data. Preferably, the structure of this model is inferred from the patient data using either the method of beta weights described in Benjamin O, Fitzgerald T H B, Ashwin P et al, *A phenomenological model of seizure initiation suggests network structure may explain seizure frequency in idiopathic generalised epilepsy. J Math Neurosci* 2012, Vol. 2, No. 1, pp. 1-41 (the contents of which are hereby incorporated by reference) or alternatively using another measure of nonlinear correlation, but, in general, the model comprises a set of nodes that correspond to brain regions of the patient brain data and connections between the nodes of the network data structure correspond to connections between the brain regions, as recorded in the source brain data. In the case of EEG data, for instance, the brain regions will correspond to regions of the brain close to the electrodes of the EEG machine.

At step 206, the application 110 generates synthetic brain activity data based on at least some of the nodes of the network model. This can be a dynamic computational model based on features of human seizure data, e.g. one that phenomenologically or physiologically models transitions from interictal to ictal states in brain regions over time, as described in the abovementioned article. In alternative embodiments, the synthetic brain activity data can be generated using a probabilistic model, for example, representation by a Markov process.

At step 208 the application 110 computes the seizure frequency from the synthetic brain activity data generation by monitoring transitions from non-seizure states to seizures states in at least some of the nodes over time. Again, techniques such as those described in the article referenced above may be used for this step. Alternatively, an analytic technique based upon the escape time of the chosen network model could be used. From a practical perspective, the seizure rate supported by the network model can be described either as the rate of transition of a specific node within the network model, an average of transitions across all nodes of the network model, or an average across all nodes of the time spent in the dynamic region corresponding to the seizure state of the model per unit of simulation time (e.g. sum the transitions observed in a time-series and divide this by the duration of the brain activity simulation).

At step 210, the application 110 uses the seizure frequency computed at step 208 to compute a likelihood of susceptibility to epilepsy/epileptic seizures in the patient, e.g. using known statistical techniques.

At step 212, the application 110 compares the likelihood computed at step 210 with another value representing a likelihood of susceptibility to epilepsy or epileptic seizures, e.g. a likelihood value computed using the above process performed on previous data obtained from the same patient. This step is then performed/repeated at a later point in time, e.g. after a period of AED treatment, in order to assess the efficacy of an AED treatment, for example, giving an indication of whether the susceptibility to epilepsy/seizures of the patient (or group of patients) has increased or decreased compared to the original baseline measurement.

Detailed examples of experiments and techniques relating to the method generalised above will now be given. A first experiment related to Idiopathic generalised epilepsy (IGE), which comprises a group of clinical syndromes which account for 15-20% of all epilepsies. Generalised spike-wave (GSW) seen with EEG is a hallmark of IGE, and reflects abnormal hypersynchronous electrical activity within brain networks; much current interest concerns the structural and functional nature of brain networks in which seizures arise and how these factors give rise to specific seizure types or epilepsy syndromes. The aim of this experiment was to use graph theory applied to EEG to explore the possibility that abnormal properties of brain networks are a component of the inherited phenotype in IGE.

The experiment involved a study of 35 patients with IGE, 42 unaffected first-degree relatives, and 40 normal controls using EEG. In one experiment the computational model described in Kalitzin S N, Velis D N, da Silva F H. *Stimulation-based anticipation and control of state transitions in the epileptic brain. Epilepsy Behav.* 2010; 17:310-323 was used to phenomenologically model the transition from interictal to ictal states in a single localized brain region. An extension of this model allowed the role of network structure in the generation of seizures to be explored. This previous study showed that a significantly higher frequency of events occurred in model networks inferred from the EEG of patients with IGE than in those where networks were calculated from healthy subjects' EEG. The present inventors hypothesised that models based on networks inferred from unaffected relatives would also have an abnormal tendency to develop seizures, and that therefore an inherited network endophenotype is part of the causal mechanism of seizures in IGE.

For MRI data, the inventors adopted methods to define nodes on the basis of parcellating grey-matter regions (see, for example, van Wijk B C, Stam C J, Daffertshofer A. *Comparing brain networks of different size and connectivity density using graph theory. PLoS One.* 2010; 5(10):e1370). Identical parcellation schemes were applied to structural T1-weighted data, to DTI, and to fMRI. Edges were defined according to MRI modality: In T1-weighted structural MRI data, pairwise correlations between thicknesses of cortex in different brain regions was estimated across subject groups, and these pairwise correlations between all available pairs of regions were used to create a graph (see He Y, Chen Z J, Evans A C. Small-world anatomical networks in the human brain revealed by cortical thickness from MRI. Cereb Cortex. 2007 Oct.; 17(10):2407-19). In fMRI data, pairwise interdependencies between the timeseries in each structural region were calculated (see Honey C J, Sporns O, Cammoun L, et al. *Predicting human resting-state functional connectivity from structural connectivity. Proc Natl Acad Sci USA.* 2009 Feb. 10; 106(6):2035-40); as with EEG, the inventors examined a range of interdependence measures. For DTI the inventors used whole-brain tractography and a measure of fibre connection density between regions (see Zhang Z, Liao W, Chen H, et al. *Altered functional-structural coupling of large-scale brain networks in idiopathic generalized epilepsy. Brain.* 2011 October; 134(Pt 10):2912-28). For each graph type, the inventors compared between subjects local node properties (e.g. measures of hub features) and global network parameters (e.g. clustering, path length, small world index, modularity) between subjects. Appropriate steps were taken to normalise network measures for null networks with appropriately similar characteristics. Additionally, to methods requiring thresholding edges, the inventors implemented the network-based statistic (NBS) method of Zalesky A, Fornito A, Bullmore E T. *Network-based statistic: identifying differences in brain networks. Neuroimage.* 2010 December; 53(4):1197-207. This method compares each pairwise connection across subjects, identifying all of the differences in a univariate sense; NBS uses an approach analogous to cluster-level statistics in SPM, to identify connected subnetworks that differ between subjects.

The present inventors discovered that in their phenomenological model, brain networks based on EEG from normal subjects are least likely to generate seizures, whereas networks based on EEG from patients or relatives are significantly more likely to generate seizures. The inventors concluded that an inherited brain network endophenotype mechanistically predisposes a subject to seizure initiation in IGE.

In the experiment subjects with IGE were identified from five hospitals in London and outlying regions, and were a consecutive series who met the inclusion and exclusion criteria and were able to participate. Inclusion criteria for patients were age >18 years old, a diagnosis of IGE, and family members with epilepsy according to self-report, (confirmed by investigations in 16/28 families). Clinically unaffected first degree relatives were recruited via subjects with IGE. Healthy participants with no personal or family history of neurological or psychiatric diseases were recruited via a local research participant database. Participants were excluded if they had any other neuropsychiatric condition or a full scale IQ (FSIQ)<70.

All EEG data were collected at a single centre. Conventional 10-20 scalp EEG was collected in the modified Maudsley configuration using a NicoletOne recording system (Viasys Healthcare, San Diego, Calif., USA), sampling rate 256 Hz, bandpass filtered 0.3-70 Hz. Ten minutes of awake EEG was obtained in all participants and 40 minutes of sleep was obtained where possible. Where specific consent was obtained, hyperventilation and photic stimulation were carried out. The EEGs were reviewed independently by two reviewers and the following features were noted: presence of GSW; focal abnormalities including spikes, sharp waves and slow waves; response to photic stimulation; and normal variants.

For the quantitative EEG analysis, a single 20s epoch was selected which included continuous dominant background rhythm with eyes closed, without any artefacts, epileptiform abnormalities or patterns indicating drowsiness or arousal. Epoch selection for analysis was carried out by one investigator who was blinded to subject group. These EEG epochs were used for all the subsequent analysis methods described below. The analyses used 5 conventional broad frequency bands: delta (1-3 Hz), theta (4-8 Hz), alpha (9-14 Hz), beta (15-30 Hz) and gamma (31-70 Hz). Although the analysis was focussed on network measures, the EEG power spectrum was also analysed. The known Welch's method was used, as implemented in the Matlab function pwelch. The spectra had a frequency resolution of 0.5 Hz. Peak frequency and power were calculated for each channel and for each frequency band and averaged over all electrodes.

To develop a phenomenological model of seizure emergence from network structure, simulations were performed with networks obtained from EEG of these subjects to determine whether the network represented was prone to seizure initiation using a model. For the purposes of these simulations, networks were obtained from the PLF matrices in a different way from the matrices described above. Directed graphs were obtained from the inverse PLF matrix in a manner analogous to obtaining the matrix of beta weights from a Pearson correlation matrix. That is, if $R=PLF^{-1}$, then define a matrix, A, where $$A_{ij} = \frac{-R_{ij}}{R_{ii}}.$$

The inventors took the matrix A as the adjacency matrix for a weighted, directed graph and obtain an unweighted, directed graph in the same manner as above. They used K values of 11, 12, 13 and 14. The unweighted, directed graph was used in a network simulation of the model with a simulation of duration 20 minutes. The number of seizures occurring during each simulation was counted so that the seizure rate could be estimated, for each network. These rates were averaged over the 4 values of K to obtain a rate for a particular subject and frequency band.

Statistical comparisons between groups were carried out in SPSS 15.0 for Windows™. Differences in the proportions of each group showing qualitative EEG abnormalities were investigated using the Chi-squared test with a significance threshold of p=0.05 two-tailed, Bonferroni-corrected for three between-group comparisons. Before testing, all quantitative measures were first tested for normality. Since these measures were not normally distributed, non-parametric Kruskal-Wallis test was used to examine for effects in each measure across the three groups and five frequency bands; results were declared significant at p<0.05 two-tailed, Bonferroni corrected for five frequency bands. Where the Kruskall-Wallis test was significant, the inventors investigated further using Mann-Whitney tests to compare between pairs of groups for each frequency band. Results were declared significant when p<0.05 after Bonferroni correction for three between-group comparisons. Where they observed a significant effect in the Kruskall-Wallis test but Mann-Whitney paired tests were not significant after Bonferroni correction, they reported as trends any findings where p<0.05 without Bonferroni correction. The inventors tested the hypothesis that seizure rates in the network model will differ between the groups.

Following examination of this a priori hypothesis, the inventors also split the patient group into two, comparing seizure-free patients and patients with ongoing seizures.

The experiment involved a study of 117 participants: 40 normal controls (20 female, mean age 30.7 yrs), 35 patients with IGE (21 female, mean age 34.4 yrs), and 42 first-degree relatives of patients with IGE (19 female, mean age 36.0 yrs). Nineteen of the patients had been seizure free for 1 year or more. The age and gender distributions of the groups were not significantly different (all p>0.05 uncorrected). Only two of the 117 subjects did not achieve sleep during the recording; 13 patients and 8 relatives refused photic stimulation because of the risk of provoking a seizure.

Seizure rates in model networks based on gamma bands show higher seizure rates in patients and relatives compared to normals. Seizure rates are higher in patients with ongoing seizures compared to normals subjects.

In terms of a network model of seizure initiation, seizure rates were higher in patients and relatives than normal controls in the gamma band (Kruskall Wllis p=0.027 corrected). Examining paired comparisons between groups, seizure rate was higher in relatives than controls (p=0.0031 corrected). There was a trend towards a higher seizure rate in patients compared to controls (p=0.047 uncorrected). There were no significant differences between patients and relatives in any frequency band. In the gamma band, there was a trend towards a higher seizure rate in the patient group with ongoing seizures compared with controls (p=0.018 uncorrected). There was no difference between the seizure-free patients and the control group.

The inventors' network model revealed that, in the beta band, the specific network structure of normal subjects was least prone to allow sudden transitions to generalised seizure-like activity; whereas patients' and relatives' network structures were significantly more prone to generate seizure-like activities.

The parameters of the network model were set to allow seizure activity to be generated within the period of simulation. These parameters therefore gave rise to a high rate of seizure occurrence in abnormal networks, and a non-zero seizure occurrence rate in normal networks. It will be appreciated that parameter ranges could be altered to produce a more realistic seizure-occurrence rate, although this would still be non-zero, in normal subjects. It is also noted that seizure occurrence in subjects who do not have epilepsy is indeed non-zero, and such seizures may be provoked by a range of factors. The seizure rate measure used herein might be best conceptualised as a measure of risk of seizure onset for a given network. It is likely that there must be multiple mechanisms which result in seizure risk and which protect from seizures—indeed this is evident in the data, since relatives have a high seizure risk, yet at the point of study had not had seizures.

The inventors' network analyses were carried out in "sensor space"—that is, networks were constructed which described the interactions between activities at the EEG electrodes, rather than the interactions between the brain sources which generated these activities. The limited spatial sampling of EEG would not readily permit source reconstruction, but other embodiments can attempt to identify the origins of these network properties in the brain.

The inventors used the experiment to show the existence of a brain network endophenotype of IGE, present in relatives and patients. Furthermore, they found that some features of brain networks differed significantly between patients with ongoing seizures and seizure-free patients. They also demonstrated in a computational model that this specific network endophenotype is prone to generate seizures, compared to normal brain networks. Hence they linked together the identification of a brain network endophenotype with a mechanistic explanation for why these abnormal networks allow seizures to emerge. Their findings have significant implications for the current mechanistic understanding of IGE, and for future phenotyping and genetics studies.

Thus, the inventors have investigated the brain network basis of common epilepsies, bringing together methods from connectomics and the mathematical theory and computational methods of dynamical systems. They investigated the dynamics of brain networks, from the perspective of complex nonlinear systems modelling, and relate the findings to recent proposals that certain epilepsies emerge from aberrant dynamics of specific brain systems.

The invention claimed is:

1. A computer-implemented system adapted to assist with assessing susceptibility to epilepsy and/or epileptic seizures in a patient, the system including:
    processor and processing application (104, 110) configured to receive (202), via an interface, patient brain data and programmed to:
    generate (204) a network model from the received patient brain data, wherein nodes in the network model correspond to brain regions of the patient brain data and connections between the nodes of the network model correspond to measured connections between the brain regions;
    generate (206) synthetic brain activity data in at least some of the nodes of the network model;
    compute (208) seizure frequency from the synthetic brain activity data by monitoring transitions from non-seizure states to seizure states in at least some of the nodes over time;
    use the seizure frequency to compute (210) a likelihood of susceptibility to epilepsy and/or epileptic seizures in the patient;
    compare (212) the computed likelihood with another likelihood of susceptibility to epilepsy and/or epileptic seizures in order to assess whether the likelihood has increased or decreased, and output data representative thereof,
    and
    a display for displaying information representative of said output data.

2. A system according to claim 1, wherein the synthetic brain activity data describes a transition of the at least some of the nodes of the network model from interictal to ictal states.

3. A system according to claim 1, wherein the network model includes a discrete set of nodes with irregular directional connectivity, where properties of each said node of the discrete set of nodes are described by a mathematical equation that simultaneously permits a normal resting state and a high-amplitude oscillatory state.

4. A system according to claim 1, wherein the patient brain data comprises electroencephalogram ("EEG") data and the nodes of the network model are based on interdependencies between EEG signals from different recording electrodes or brain regions.

5. A system according to claim 1, wherein the patient brain data comprises magnetic resonance imaging ("MRI") data and the nodes of the network model are based on parcellating grey-matter regions of the patient brain data.

6. A system according to claim 1, wherein the patient brain data comprises MRI data and the nodes of the network model are based on interdependencies between MRI signals from different brain regions.

7. A system according to claim 1, wherein the network model is inferred from the patient data using a beta weights method, or by using a measure of nonlinear correlation.

8. A system according to claim 1, wherein the synthetic brain activity data is generated (206) using a dynamic computational model based on features of human seizure data that phenomenologically or physiologically models transitions from interictal to ictal states in brain regions over time.

9. A system according to claim 1, wherein the synthetic brain activity data is generated (206) using a probabilistic model.

10. A system according to claim 1, wherein the seizure frequency describes a rate of transition of a node of at least some of the nodes within the network model.

11. A system according to claim 1, wherein the seizure frequency is based on an average of transitions across all said nodes of the network model per unit of synthetic brain activity data generation time.

12. A system according to claim 1, wherein the seizure frequency is based on an average value across all nodes of time spent in a dynamic region corresponding to the seizure states of the model per unit of synthetic brain activity data generation time.

13. A system according to claim 1, wherein the another likelihood corresponds to a historical computed likelihood.

14. A system according to claim 13, wherein the likelihood compared with the historical likelihood was computed following the patient receiving automated external defibrillator ("AED") treatment.

15. A non-transitory computer program element (110) comprising computer code means to make the computer execute a method of assisting with assessing susceptibility to epilepsy and/or epileptic seizures in a patient, the method including:
    receiving (202) patient brain data;
    generating (204) a network model from received patient brain data, wherein nodes in the network model correspond to brain regions of the patient brain data and connections between the nodes of the network model correspond to measured connections between the brain regions;

generating (206) synthetic brain activity data in at least some of the nodes of the network model;

computing (208) seizure frequency from the synthetic brain activity data by monitoring transitions from non-seizure states to seizure states in at least some of the nodes over time;

using (210) the seizure frequency to compute a likelihood of susceptibility to epilepsy and/or epileptic seizures in the patient, comparing (212) the computed likelihood with another likelihood of susceptibility to epilepsy and/or epileptic seizures in order to assess whether the likelihood has increased or decreased;

causing a display to display data representative of the computed likelihood of susceptibility to epilepsy and/or epileptic seizures in the patient.

\* \* \* \* \*